United States Patent [19]

Hesse et al.

[11] Patent Number: 5,683,492
[45] Date of Patent: Nov. 4, 1997

[54] PROCESS FOR THE RECOVERY OF CARBON MONOXIDE FROM A PURGE GAS CONTAINING AT LEAST CARBON MONOXIDE, NITROGEN AND HYDROGEN

[75] Inventors: Peter Hesse, München; Siegfried Michel, Egling; Horst Weiss, München, all of Germany

[73] Assignee: Linde Aktiengesellschaft, Wiesbaden, Germany

[21] Appl. No.: 653,296

[22] Filed: May 24, 1996

[30] Foreign Application Priority Data

May 24, 1995 [DE] Germany ............ 195 19 197.8

[51] Int. Cl.$^6$ ............ B01D 53/47; B01D 53/14
[52] U.S. Cl. ............ 95/92; 95/94; 95/96; 95/127; 95/130; 95/140; 95/233; 95/237
[58] Field of Search ............ 95/92–96, 127, 95/130, 140, 148, 233, 237; 562/607, 608

[56] References Cited

U.S. PATENT DOCUMENTS

| | | | |
|---|---|---|---|
| 3,186,145 | 6/1965 | Pelton et al. | 95/237 X |
| 3,699,218 | 10/1972 | Smith et al. | 95/92 X |
| 4,255,591 | 3/1981 | Makin et al. | 562/517 |
| 4,299,596 | 11/1981 | Benkmann | 95/100 |
| 4,316,880 | 2/1982 | Jockel et al. | 95/140 X |
| 4,755,361 | 7/1988 | Fuderer | 95/96 X |
| 4,778,670 | 10/1988 | Pinto | 95/96 X |
| 4,846,851 | 7/1989 | Guro et al. | 95/140 X |
| 4,861,351 | 8/1989 | Nicholas et al. | 95/140 X |
| 5,096,470 | 3/1992 | Krishnamurthy | 95/140 X |
| 5,112,590 | 5/1992 | Krishnamurthy et al. | 95/140 X |

FOREIGN PATENT DOCUMENTS

| | | | |
|---|---|---|---|
| 0307843 | 3/1989 | European Pat. Off. | 95/92 |
| 0367618 | 5/1990 | European Pat. Off. | 95/140 |
| 0563702 | 10/1993 | European Pat. Off. | 95/96 |
| 2538121 | 3/1977 | Germany | 95/233 |
| 60-155519 | 8/1985 | Japan | 95/96 |
| 61-077616 | 4/1986 | Japan | 95/96 |
| 3-242313 | 10/1991 | Japan | 95/96 |
| 4-200713 | 7/1992 | Japan | 95/140 |
| 5-023523 | 2/1993 | Japan | 95/96 |
| 5-023524 | 2/1993 | Japan | 95/96 |
| 5-253436 | 10/1993 | Japan | 95/96 |
| 6-126121 | 5/1994 | Japan | 95/96 |
| 2127710 | 4/1984 | United Kingdom | 95/140 |
| 2275625 | 9/1994 | United Kingdom | 95/92 |

OTHER PUBLICATIONS

UK Search Report dated Aug. 15, 1996.

Abstract, Derwent WPI, JP 07278043 A, Oct. 24, 1995, Week 9551.

Inpadoc Search/Fam. & Legal Stat. 1996/UD–9637, File 345.

*Primary Examiner*—Robert Spitzer
*Attorney, Agent, or Firm*—Millen, White, Zelano, & Branigan, P.C.

[57] ABSTRACT

A process for the recovery of carbon monoxide from a purge gas from acetic acid synthetic containing at least carbon monoxide, nitrogen and hydrogen, wherein the purge gas (6) containing at least carbon monoxide, nitrogen and hydrogen is separated into a gas fraction (11) rich in carbon monoxide and a residual gas fraction (12, 13) rich in nitrogen and hydrogen by an adsorption process (G), preferably by a pressure change absorption process, and the gas fraction (11) rich in carbon monoxide is returned upstream of the acetic acid.

13 Claims, 1 Drawing Sheet

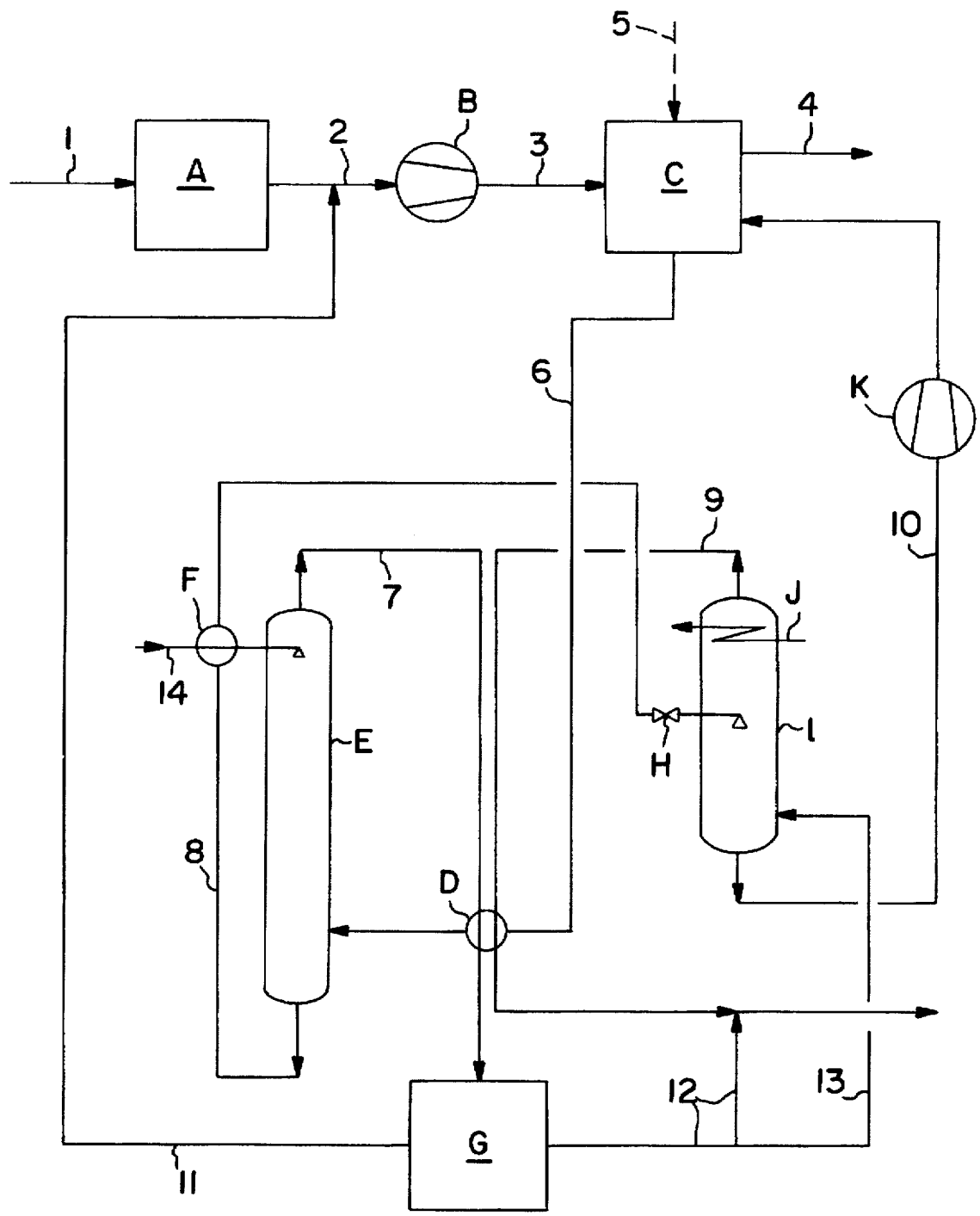

PROCESS FOR THE RECOVERY OF CARBON MONOXIDE FROM A PURGE GAS CONTAINING AT LEAST CARBON MONOXIDE, NITROGEN AND HYDROGEN

BACKGROUND OF THE INVENTION

The present invention relates to process gas recovery, and particularly concerns a method for the recovery of carbon monoxide from a purge gas, containing at least carbon monoxide, nitrogen and hydrogen, which is produced in an acetic acid synthesis process.

Acetic acid synthesis requires highly pure carbon monoxide and methanol as charge gases. The highly pure carbon monoxide is usually obtained by means either of a cryogenic, adsorptive or membrane separation process.

In acetic acid synthesis it is necessary to discharge inert gas components, in particular nitrogen, to control the inert gas level. These inert gas components and other components such as for example acetic acid, esters, halogens, etc. are termed so-called purge gas. However, in addition, this purge gas also contains carbon monoxide, the level of carbon monoxide also being dependent on the level of the inert gases in the highly pure carbon monoxide fraction fed to the acetic acid synthesis.

Whereas it has been customary for many years to utilize this purge gas fraction for its heating value or just to burn it off, a process for recovery of the carbon monoxide from the purge gas from the acetic acid synthesis is described in EP-AP 0 013 804.

In this process for recovery of carbon monoxide from the purge gas from acetic acid synthesis, the purge gas is first freed of undesired components, such as halogens for example, in a preliminary purification stage. This preliminary purification is carried out either by adsorptive means or by means of washing. The purge gas now only containing carbon monoxide, carbon dioxide, nitrogen and hydrogen is then separated into a gas fraction rich in hydrogen and carbon dioxide and a gas fraction rich in carbon monoxide and nitrogen in a membrane separation stage. The latter is then returned before the acetic acid synthesis.

However, this process for recovery of carbon monoxide from the purge gas from the acetic acid synthesis has the great disadvantage that the inert nitrogen component is returned again together with the carbon monoxide before the acetic acid synthesis. Thus, although the carbon monoxide to be produced is reduced, on the other hand this procedure leads to enrichment of the inert nitrogen component in the acetic acid synthesis.

SUMMARY OF THE INVENTION

The object of the present invention is to provide a process for the recovery of carbon monoxide from the purge gas produced in acetic acid synthesis which prevents enrichment of the inert nitrogen component.

According to the invention this objective is achieved in that the purge gas containing at least carbon monoxide, nitrogen and hydrogen is separated into a gas fraction rich in carbon monoxide and a residual gas fraction rich in nitrogen and hydrogen by means of an adsorption process, preferably by means of a pressure swing adsorption process, and the gas fraction rich in carbon monoxide is returned before the acetic acid synthesis.

Now, with the process according to the invention, a carbon monoxide fraction which is comparatively purer, in particular in terms of nitrogen, can be obtained from the purge gas from the acetic acid synthesis and returned before the acetic acid synthesis. On the other hand, the inert nitrogen component is discharged from the installation together with other components, such as for example hydrogen, as the residual gas fraction.

Although an adsorption process, in particular a pressure swing adsorption process, is more expensive and requires more attention than the membrane separation stage described in the above European patent application, these disadvantages are more than offset by the advantages attainable with the process according to the invention.

Since, as already mentioned, the level of carbon monoxide of the purge gas is roughly dependent on the level of inert components in the carbon monoxide fraction fed to the acetic acid synthesis, the process according to the invention achieves a reduction in the quantity of purge gas since the quantity of inert gas in the carbon monoxide fraction fed to the acetic acid synthesis is reduced.

One variant of the process according to the invention is characterised in that the carbon monoxide content of the gas fraction rich in carbon monoxide is at least 98.0 mol % carbon monoxide, preferably 99.0 mol % carbon monoxide, in particular 99.5 mol % carbon monoxide.

Such carbon monoxide purity levels are possible with more recent pressure swing adsorption processes. The gas fraction rich in carbon monoxide obtained by means of the adsorption process should at least be comparable in purity to the highly pure carbon monoxide charge gas for the acetic acid synthesis.

In a development of the invention, it is proposed that undesired components in the adsorption, such as for example acetic acid, carbon dioxide, halogens, etc., are separated from the purge gas by means of an adsorption process.

Provision is also made for scrubbing out undesired components up stream of the adsorption process when these undesired components are components which would otherwise lead to contamination or damage to the adsorption bed or beds. If these undesired components in the adsorption can be returned to the acetic add synthesis, expediently provision is also made for this procedure to be carried out.

According to a further variant of the process according to the invention, methanol is fed to the scrubbing (absorption) process as a scrubbing liquid.

In certain circumstances the components separated from the purge gas by means of the absorption process and intended to be returned to the acetic acid synthesis contain components which make it undesirable to return these components to the acetic acid synthesis.

In this case the invention proposes that such components are removed by means of a stripping process.

Since a so-called stripping gas is required for this stripping process, according to a further variant of the process according to the invention, provision is made for at least one partial stream of the residual gas fraction rich in nitrogen and hydrogen obtained by means of the adsorption process to be fed to the stripping process as the stripping gas.

With this procedure this residual gas fraction rich in nitrogen and hydrogen which otherwise might only be discarded or burnt off, can be put to more efficient use.

BRIEF DESCRIPTION OF FIGURES

The invention and further variants thereof will be explained in greater detail with reference to the accompanying drawing, which shows schematically an installation for removing carbon monoxide from a purge gas, containing at least carbon monoxide, nitrogen and hydrogen, which is produced in an acetic acid synthesis process.

DETAILED DESCRIPTION OF FIGURE

Referring now to the FIGURE, a gas rich in carbon monoxide originating from a synthesis gas installation is fed through line 1 to a carbon monoxide installation A. In this installation a highly pure carbon monoxide gas is produced by means of a cryogenic or adsorptive or membrane separation process. Such a highly pure carbon monoxide gas preferably contains less than 0.5 mol % hydrogen and less than 1.5 mol % nitrogen.

The highly pure carbon monoxide gas is fed through line 2 to a compressor B and after compression through line 3 to the actual acetic acid synthesis plant C. It will be clear to the skilled man that the compression step can be carried out in one or more stages. The number of compressor stages is determined both by the outlet pressure of the carbon monoxide installation A and the desired inlet pressure of the acetic acid synthesis plant C.

The acetic acid product fraction is removed through line 4. As already mentioned, in the acetic acid synthesis process it is necessary to discharge inert gas components and hydrogen and carbon monoxide formed in the acetic acid synthesis plant C, the so-called purge gas fraction, to control the inert gas level.

This purge gas fraction is carried out of the acetic acid synthesis plant C through line 6. It is cooled in the heat exchanger D by thermal interchange with process streams to be warmed, or if necessary cooled with a further refrigerant stream to be warmed, e.g. ammonia (not shown in the FIGURE), and then fed to the lower part of the scrubbing or absorption column E.

The scrubbing or absorption column E is used to separate the purge gas fraction removed from the acetic acid synthesis plant C into a fraction rich in carbon monoxide/nitrogen and a fraction essentially containing acetic acid, methanol, carbon dioxide, halogens, etc. Methanol is fed to the top of the scrubbing column E through line 14 as scrubbing agent. Before it is introduced into the scrubbing column, the methanol is cooled in the heat exchanger F in indirect heat exchange the process stream to be warmed in line 8, which will be described further on. If necessary, here too provision is made for additional cooling with a refrigerant to be warmed, such as ammonia for example.

At the top of the scrubbing column E, a gas fraction rich in carbon monoxide/nitrogen is removed by means of line 7. This is warmed in the heat exchanger D already mentioned with the purge gas stream to be cooled, and then fed to the adsorption unit G.

An adsorptive separation process which works on the principle of pressure swing adsorption, is known for example from DE-PS 26 04 305. This adsorptive separation process for obtaining carbon monoxide from gas mixtures containing carbon monoxide is also particularly suitable for separating a carbon monoxide/nitrogen gas mixture.

Since the components possibly harmful to the adsorption media, such as for example acetic acid, hydrogen iodide, methyl iodide, etc., are already removed from the purge gas fraction in the scrubbing column E, there is now no danger whatsoever of possible damage to the adsorption media used in the adsorption installation G.

The gas stream rich in carbon monoxide obtained in the adsorption installation G is returned before the acetic acid synthesis plant C by means of line 11. Here, the gas fraction rich in carbon monoxide can be returned either as a unitary stream before the compressor 8 or as partial streams before each of the individual compressor stages in the case of multi-stage compression.

The residual gas fraction rich in nitrogen and containing hydrogen obtained in the adsorption installation G is withdrawn from adsorption installation G through line 12. The further use of this residual gas fraction is discussed in greater detail below.

A liquid fraction, essentially consisting of methanol, carbon dioxide, halogens, etc., is removed from the bottom of the scrubbing column E by means of line 8, warmed in the heat exchanger F with the methanol to be cooled, and then allowed to expand through the valve H into the stripping column I. In the stripping column I the fraction removed at the bottom of the scrubbing column E is separated into a gas fraction rich in carbon dioxide and a liquid fraction essentially consisting of methanol, halogens, etc. A part of the residual gas fraction rich in nitrogen, obtained in adsorption installation G, is fed to the stripping column I through the lines 12 and 13 as the stripping gas.

A top cooler J is provided at the top of the stripping column I for recondensation of the scrubbing medium vapours.

A gas fraction rich in carbon dioxide is removed at the top of the stripping column I through line 9, warmed in the heat exchanger D by thermal interchange with the purge gas to be cooled, and then carried out of the installation. The part of the residual gas rich in nitrogen obtained in the absorption installation G and not used as stripping gas is mixed with the gas fraction rich in carbon dioxide in line 9. This gas mixture consisting of carbon dioxide, nitrogen, hydrogen, etc. can be fed to a combustion unit for example.

The liquid fraction produced at the bottom of the stripping column I, containing mainly methanol and also containing acetic acid, halogens, etc., is removed by means of line 10, compressed in one or more stages (K) and then recycled to the acetic acid synthesis plant C.

With the described procedure, the entire methanol requirement needed for the acetic acid synthesis plant C can be covered by the methanol fed to the top of the scrubbing column E through line 14. Even so, if additional methanol should be required for the acetic acid synthesis plant C, this can be fed to the acetic acid synthesis plant C through the line 5 shown by the broken lines.

The following table gives an example for the composition of the gas fractions in the lines 2 and 3 and 6 to 14.

TABLE 1

Composition of the gas streams

| Stream/line | 2 | 3 | 6 | 7 | 8 | 9 | 10 | 11 | 12 | 13 | 14 |
|---|---|---|---|---|---|---|---|---|---|---|---|
| $H_2$ [mol %] | 0.10 | 0.10 | 10.00 | 10.84 | | 16.54 | | 0.10 | 31.12 | 31.12 | |
| $N_2$ [mol %] | 1.00 | 1.00 | 16.00 | 17.34 | | 25.63 | | 1.00 | 48.20 | 48.20 | |
| CO [mol %] | 98.90 | 98.90 | 66.18 | 71.14 | | 10.99 | | 98.78 | 20.68 | 20.68 | |
| $CO_2$ [mol %] | | 0.0004 | 7.00 | 0.02 | 0.15 | 46.42 | 0.03 | 0.03 | | | |
| $CH_3OH$ [mol %] | | 0.001 | | 0.06 | 99.83 | 0.42 | 99.95 | 0.09 | | | 100.00 |
| Acetic acid [mol %] | | | 0.80 | | 0.017 | | 0.017 | | | | |
| Ester [mol %] | | | 0.02 | | 0.0004 | | 0.0004 | | | | |
| $CH_3J$ [mol %] | | | 0.0005 | | 0.0001 | | 0.0001 | | | | |
| Flow rate [kmol/h] | 4540 | 4600 | 100 | 92.25 | 4608 | 12 | 4602 | 60.3 | 25.6 | 6.4 | 4600 |
| Pressure [bar] | 1 | 30 | 12.0 | 11.0 | 11.0 | 1.1 | 1.1 | 1.0 | 2.0 | 2.0 | 12.0 |
| Temperature [K] | 303 | 303 | 303 | 293 | 293 | 293 | 290 | 303 | 298 | 298 | 303 |

As to the specific details of the PSA process that is preferred for the invention, attention is invited to U.S. Pat. No. 4,299,596 issued Nov. 10, 1981, which is the counterpart of DE-PS2604305.

Another useable PSA process is described in the article "Adsorption CO-recovery from Steelwork Waste Gates", published in LINDE-Reports on Science and Technology, No. 44 (1988). As known to those working in the field, there exists a multitude of synthetic zeolites that can be used for a PSA-process of this kind. The choice of the specific synthetic zeolite will depend on the specific composition of the gas stream to be treated. But this choice lies within the knowledge of a person of ordinary skill in the field.

It should also be mentioned that it would be possible to use an adsorption process without a pressure relief for the purpose of regeneration.

Contaminants which might damage the adsorption bed(s) include, for example: $CO_2$, acetic acid, halogens, especially hydrogen iodide and methyl iodide. These contaminants are normally included in the "feed gas stream".

Components which should not be recycled to the acetic acid synthesis include, for example, $CO_2$, $N_2$, $H_2$ and $CH_4$. Therefore, these components are withdrawn from the stripping column (I) via conduit 9. However, the main part of the gaseous fraction withdrawn via conduit 9 is $CO_2$, while only traces of $N_2$, $H_2$ and $CH_4$ are included in this gaseous fraction.

The preceding examples can be repeated with similar success by substituting the generically or specifically described reactants and/or operating conditions of this invention for those used in the preceding examples.

The entire disclosure of all applications, patents and publications, cited above and below, and of corresponding German application 19519197.8, are hereby incorporated by reference.

From the foregoing description, one skilled in the art can easily ascertain the essential characteristics of this invention, and without departing from the spirit and scope thereof, can make various changes and modifications to adapt it to various usages and conditions.

We claim:

1. A process for recovering carbon monoxide from a purge gas stemming from an acetic acid synthesis stage, said process comprising: withdrawing from said acetic acid synthesis stage a purge gas (6) containing at least carbon monoxide, nitrogen and hydrogen, subjecting said purge gas to an adsorption process (G) to separate said purge gas into a gas fraction (11) rich in carbon monoxide and a residual gas fraction (12, 13) rich in nitrogen and hydrogen, and recycling the gas fraction (11) rich in carbon monoxide upstream of the acetic acid synthesis stage (C).

2. A process according to claim 1, wherein the carbon monoxide content of the gas fraction (11) rich in carbon monoxide is at least 98.0 mol % carbon monoxide.

3. A process according to claim 1 further comprising, upstream of said adsorption process, subjecting the purge gas to an absorption process (E) to remove undesired components comprising acetic acid, carbon dioxide, and a halogen, in a scrubbing liquid.

4. A process according to claim 3, wherein methanol (14) is the scrubbing liquid.

5. A process according to claim 4, further comprising stripping the scrubbing liquid containing the undesired components with a stripping gas to form a fraction (9) rich in carbon dioxide and a liquid methanolic fraction (10) containing mainly methanol and also containing acetic acid and halogen.

6. A process according to claim 5, wherein the residual gas fraction (12, 13) rich in nitrogen and hydrogen obtained from the adsorption process (G) is fed to the stripping process (I) as the stripping gas.

7. A process according to claim 6, wherein the adsorption process is a pressure swing adsorption process.

8. A process according to claim 3, wherein the adsorption process is a pressure swing adsorption process.

9. A process according to claim 4, wherein the adsorption process is a pressure swing adsorption process.

10. A process according to claim 5, wherein the adsorption process is a pressure swing adsorption process.

11. A process according to claim 1, wherein the adsorption process is a pressure swing adsorption process.

12. A process according to claim 1, wherein the carbon monoxide content of the gas fraction (11) rich in carbon monoxide is at least 99.0 mol % carbon monoxide.

13. A process according to claim 1, wherein the carbon monoxide content of the gas fraction (11) rich in carbon monoxide is at least 99.5 mol % carbon monoxide.

* * * * *